United States Patent
Nishiyama et al.

(10) Patent No.: US 11,332,612 B2
(45) Date of Patent: May 17, 2022

(54) POLYHYDROXYALKANOATE PARTICLES AND AQUEOUS DISPERSION OF SAME

(71) Applicant: KANEKA CORPORATION, Osaka (JP)

(72) Inventors: Kazuki Nishiyama, Takasago (JP); Tomoaki Ashida, Takasago (JP)

(73) Assignee: KANEKA CORPORATION, Osaka (JP)

( * ) Notice: Subject to any disclaimer, the term of this patent is extended or adjusted under 35 U.S.C. 154(b) by 303 days.

(21) Appl. No.: 16/500,306

(22) PCT Filed: Mar. 29, 2018

(86) PCT No.: PCT/JP2018/013238
§ 371 (c)(1),
(2) Date: Oct. 2, 2019

(87) PCT Pub. No.: WO2018/186278
PCT Pub. Date: Oct. 11, 2018

(65) Prior Publication Data
US 2021/0054191 A1    Feb. 25, 2021

(30) Foreign Application Priority Data
Apr. 5, 2017 (JP) .............................. JP2017-075282

(51) Int. Cl.
C08L 1/00 (2006.01)
C08L 3/00 (2006.01)
C08L 67/04 (2006.01)

(52) U.S. Cl.
CPC ........... *C08L 67/04* (2013.01); *C08L 2207/53* (2013.01)

(58) Field of Classification Search
CPC .... C08L 67/04; C08L 2207/53; C08L 101/16; C08L 5/00; C08L 1/00; C08L 3/00; C12P 7/625
USPC ...................................................... 523/205
See application file for complete search history.

(56) References Cited

U.S. PATENT DOCUMENTS

| | | | |
|---|---|---|---|
| 5,711,842 A | 1/1998 | Kemmish | |
| 6,228,934 B1 | 5/2001 | Horowitz et al. | |
| 7,435,567 B2 * | 10/2008 | Osakada | C12M 47/06 435/135 |
| 2005/0196827 A1 | 9/2005 | Osakada et al. | |
| 2013/0225761 A1 * | 8/2013 | Whitehouse | C08L 67/04 524/599 |

FOREIGN PATENT DOCUMENTS

| | | | |
|---|---|---|---|
| JP | 9-500157 A | 1/1997 | |
| WO | WO-9533064 A1 * | 12/1995 | ............. C12P 7/625 |
| WO | WO 97/21762 A1 | 6/1997 | |
| WO | WO 2005/085461 A1 | 9/2005 | |
| WO | WO 2011/116681 A1 | 10/2010 | |

OTHER PUBLICATIONS

Extended European Search Report dated Dec. 11, 2020 in corresponding European Patent Application No. 18780481.0, 11 pages.
International Search Report dated Jun. 26, 2018 in PCT/JP2018/013238 filed Mar. 29, 2018.
Dong, Zhaolin, et al., "A new method of recovering polyhydroxyalkanoate from *Azotobacter chroococcum*," Chinese Science Bulletin, vol. 45, No. 3, Feb. 2000, pp. 252-256.

* cited by examiner

*Primary Examiner* — Hannah J Pak
(74) *Attorney, Agent, or Firm* — Oblon, McClelland, Maier & Neustadt, L.L.P.

(57) ABSTRACT

Provided are PHA particles which are excellent in dispersibility in an aqueous dispersion and have excellent film formation capability, in which odor of a molded body obtained from the PHA particles or an aqueous dispersion of the PHA particles is suppressed, and whose color tone is good, and an aqueous dispersion of the PHA particles. Polyhydroxyalkanoate particles including polyhydroxyalkanoate having a particle shape and peptidoglycan covering a portion of or an entire surface of the polyhydroxyalkanoate. In this polyhydroxyalkanoate particle, a content of polyhydroxyalkanoate is 98.0% by weight or more, and a content of peptidoglycan is 0.1% by weight or more and 1.0% by weight or less.

11 Claims, 2 Drawing Sheets

POLYHYDROXYALKANOATE PARTICLES AND AQUEOUS DISPERSION OF SAME

TECHNICAL FIELD

The present invention relates to polyhydroxyalkanoate particles and an aqueous dispersion in which the particles are dispersed in an aqueous medium.

BACKGROUND ART

Polyhydroxyalkanoate (hereinafter sometimes referred to as PHA) is known as a resin which can be produced by bacteria and plants. In such PHA, the raw material is plant-derived, and the PHA has excellent biodegradability; therefore, various attempts have been vigorously made to use the PHA as an environmentally friendly plastic material.

As an attempt to use PHA as a plastic material, use in the form of an aqueous dispersion (emulsion) of PHA has been studied. For example, PTL 1 discloses a method in which PHA is dissolved in an organic solvent and then extruded together with a surfactant, PVA and the like to produce an aqueous dispersion. For example, PTL 2 discloses a method in which a slurry containing a polymer containing low crystallinity or amorphous PHA dispersed in high pressure homogenizer is heated above the melting point of the polymer and then cooled to produce a PHA dispersion. PTL 3 discloses a method of adding a water-soluble copolymer in order to disperse PHA particles.

CITATION LIST

Patent Literature

PTL 1: U.S. Patent Application Publication No. 2013/0225761
PTL 2: U.S. Pat. No. 6,228,934
PTL 3: International Publication No. 1997/021762

SUMMARY OF INVENTION

Technical Problem

However, in the conventional methods as described in PTLS 1 and 2, the use of an organic solvent may increase environmental burden, or the addition of a dispersant may impair product quality. In addition, it is disadvantageous in terms of energy because previously purified PHA is used, and then a slurry containing PHA is repeatedly heated and cooled to obtain an emulsion. In the method described in PTL 3, a dispersant in a certain concentration or more is necessary to prevent aggregation of PHA particles, and inherent biodegradability of PHA may be impaired, or odor and color tone may deteriorate during heating.

Therefore, an object of the present invention is to provide PHA particles which are excellent in dispersibility in an aqueous dispersion and have excellent film formation capability, in which odor of a molded body obtained from the PHA particles or an aqueous dispersion of the PHA particles is suppressed, and whose color tone is good; and an aqueous dispersion of the PHA particles.

Solution to Problem

As a result of intensive studies to solve the above problems, the present inventors have found that according to the PHA particles having peptidoglycan on a portion of or the entire surface in which the amount of PHA and the amount of peptidoglycan are controlled within a specific range, it is possible to obtain an emulsion (aqueous dispersion) in which the PHA particles are stably dispersed in water without aggregation. The present inventors have further found that the aqueous dispersion is excellent in film formation capability, and a molded body produced using the aqueous dispersion or the PHA particles has suppressed odor and an excellent color tone. The present invention is an invention completed based on these findings. The present inventors have furthermore found that a PHA aqueous dispersion of the present invention has excellent film formation capability not only in the case of crystalline PHA having a relatively high degree of crystallinity but also in the case of low crystallinity PHA or amorphous PHA.

That is, the present invention relates to, for example, the following inventions.

[1] Polyhydroxyalkanoate particles including polyhydroxyalkanoate having a particle shape and peptidoglycan covering a portion of or an entire surface of the polyhydroxyalkanoate, in which a content of polyhydroxyalkanoate is 98.0% by weight or more, and a content of peptidoglycan is 0.1% by weight or more and 1.0% by weight or less.
[2] The polyhydroxyalkanoate particles according to [1], in which a protein content is 1.0% by weight or less.
[3] A polyhydroxyalkanoate aqueous dispersion including an aqueous medium and the polyhydroxyalkanoate particles according to [1] or [2] dispersed in the aqueous medium.
[4] The polyhydroxyalkanoate aqueous dispersion according to [3], in which an average particle size of the polyhydroxyalkanoate particles dispersed in the aqueous medium is 0.05 µm or more and 10 µm or less.

Advantageous Effects of Invention

Since the PHA particles of the present invention have the above-mentioned constitution, an aqueous dispersion (emulsion) in which the particles are dispersed in water without aggregation is obtained, and by using the emulsion, a molded body such as a good PHA film having suppressed odor and an excellent color tone can be formed. In the emulsion, even when the PHA particles are precipitated by long-term storage, the PHA particles can be disassembled by simple stirring such as shaking and can be easily redispersed.

DESCRIPTION OF EMBODIMENTS

Figure 1:
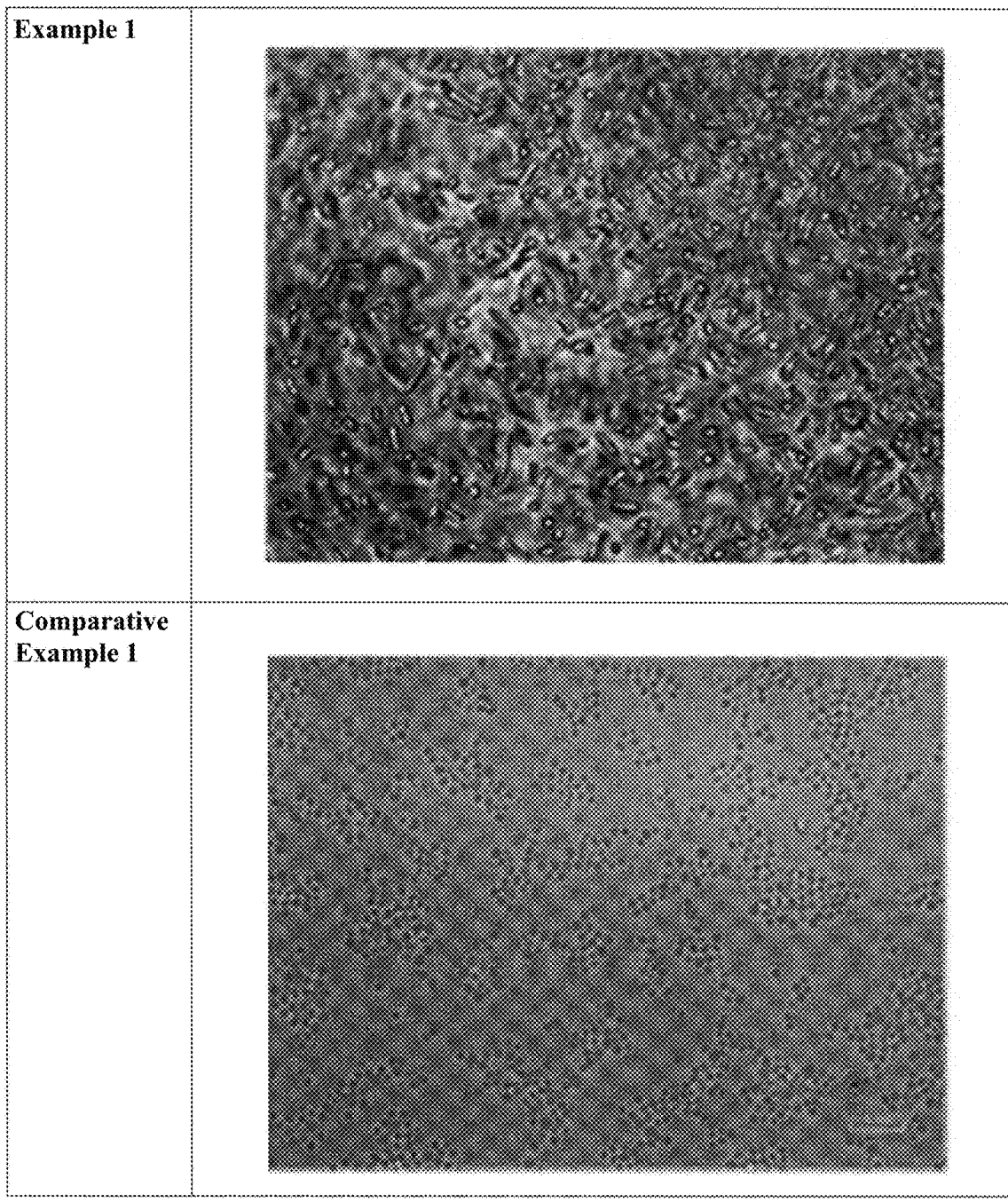
FIG. 1 is photographs of diluted products of aqueous dispersions prepared in Example 1 and Comparative Example 1.

[Polyhydroxyalkanoate Particles]
The PHA particles of the present invention are particles having at least particulate PHA and peptidoglycan covering a portion of or the entire surface of the PHA.
(A) Polyhydroxyalkanoate (PHA)
PHA constituting the PHA particles of the present invention is a polymer constituted with hydroxyalkanoic acid as a monomer component. Especially, PHA is preferably microbially produced PHA produced from a microorganism in terms of easily obtaining the PHA particles of the present invention and more preferably microbially produced PHA (aliphatic polyester) containing a repeating unit represented by the following general formula (1):

[—CHR—CH$_2$—CO—O—]   (1)

where R is an alkyl group represented by $C_nH_{2n+1}$ and n is an integer of 1 or more and 15 or less.

PHA is generally classified into the above-mentioned microbially produced PHA and chemically synthesized PHA obtained by chemical synthesis such as ring-opening polymerization of lactone. These PHAs have different structures, and in the microbially produced PHA, a monomer structural unit thereof includes only D-form (R-form), and the microorganism-produced PHA has optical activity. On the other hand, in the chemically synthesized PHA, monomer structural units derived from D-form (R-form) and L-form (S-form) are randomly bonded, and the chemically synthesized PHA is optically inactive.

As PHA, PHA containing a 3-hydroxybutyrate unit is preferable, and as such PHA, for example, poly(3-hydroxybutyrate) (PHB), poly(3-hydroxybutyrate-co-3-hydroxyvalerate) (PHBV), [poly(3-hydroxybutyrate-co-3-hydroxyvalerate-co-3-hydroxyhexanoate) (P3HB3HV3HH), poly(3-hydroxybutyrate-co-3-hydroxyhexanoate) (PHBH), poly(3-hydroxybutyrate-co-4-hydroxybutyrate) (P3HB4HB), poly(3-hydroxybutyrate-co-3-hydroxyoctanoate), poly(3-hydroxybutyrate-co-3-hydroxyoctadecanoate), and the like are preferable from the viewpoint of easiness in industrial production. Among these, PHB, PHBV, P3HB3HV3HH, PHBH, and P3HB4HB are particularly preferable. When PHA is a PHA containing a 3-hydroxybutyrate unit structure, from the viewpoint of the balance between flexibility and strength, an average composition ratio of repeating units (monomer structural units) is preferably such that a composition ratio of poly(3-hydroxybutyrate) is 60 mol % to 99 mol %, more preferably 70 mol % to 99 mol %, still more preferably 80 mol % to 99 mol %, and yet further preferably 85 mol % to 97 mol %.

Examples of low crystallinity PHA or amorphous PHA include PHA with a degree of crystallinity of 30% or less, as described in the literature: Y Doi, S. Kitamura, H. Abe, Macromolecules, 28, pp. 4822-4828 (1995). As low crystallinity PHA or amorphous PHA, more specifically, in the PHBH, PHBH in which a composition ratio of 3-hydroxyhexanoate (hereinafter abbreviated as "3HH") is 15 mol % or more is suitably used. For example, when the composition ratio of 3HH is 15 mol %, the degree of crystallinity is 26±5%. As the composition ratio of 3HH increases, the degree of crystallinity decreases, and when a 3HH composition ratio is 25 mol %, the degree of crystallinity is 18±5%. When the 3HH composition ratio exceeds 15 mol %, adhesion of PHBH particles is enhanced, and when the 3HH composition ratio is 25 mol %, PHBH particles become gum like at room temperature. Although the degree of crystallinity can usually change with time or depending on the environment etc., the degree of crystallinity described in the above-mentioned literature means a maximum value of the degree of crystallinity that can be taken.

PHA in the PHA particles of the present invention can be produced by a known or conventional method. When PHA is microbially produced PHA, the microorganisms used for producing the PHA are not particularly limited as long as they have the ability to produce PHAs. For example, *Bacillus megaterium* is a first poly(3-hydroxybutyrate) (hereinafter abbreviated as "PHB")-producing microorganism discovered in 1925, and natural microorganisms such as *Cupriavidus necator* (formerly classified as *Alcaligenes eutrophus*, or *Ralstonia eutropha*) and *Alcaligenes latus* are known as other PHB-producing microorganisms. These microorganisms accumulate PHB in their cells.

Further, known microorganisms that produce copolymers including a hydroxybutyrate unit and another hydroxyalkanoate unit are, for example, *Aeromonas caviae* that produces poly(3-hydroxybutyrate-co-3-hydroxyvalerate) and poly(3-hydroxybutyrate-co-3-hydroxyhexanoate), and *Alcaligenes eutrophus* that produces poly(3-hydroxybutyrate-co-4-hydroxybutyrate). Particularly, a preferred PHBH-producing microorganism is, for example, *Alcaligenes eutrophus* AC32 (FERM BP-6038 (T. Fukui, Y Doi, J. Bateriol., 179, p. 4821-4830 (1997)) produced by introducing a PHA synthase gene to improve PHBH productivity. These microorganisms are cultured under appropriate conditions, and the thus obtained cells having PHBH accumulated therein are used. Other than the above microorganisms, genetically-modified microorganisms may also be used which are produced by introducing various PHA synthesis-related genes depending on the desired type of PHA to be produced. In this case, culture conditions including the type of a substrate may be optimized.

In the PHA particles of the present invention, one kind of PHA may be used alone, or two or more kinds thereof may be used in combination.

The content of PHA in the PHA particles of the present invention is 98.0% by weight or more, preferably 98.5% by weight or more, and more preferably 99.0% by weight or more based on 100% by weight of the PHA particles. The upper limit of the content of PHA is not particularly limited, but is preferably 99.9% by weight or less, more preferably 99.8% by weight or less, and still more preferably 99.5% by weight or less. By setting the content of PHA to 98.0% by weight or more, melt processing is easily performed, and a molded body with reduced odor at the time of heat molding can be obtained. On the other hand, by setting the content of PHA to 99.9% by weight or less, the amount of peptidoglycan can be secured to a certain degree, and the dispersibility of the PHA aqueous dispersion tends to be further improved. The content of PHA in the PHA particles of the present invention can be determined, for example, by a gas chromatograph or TG-DTA, and more specifically, the PHA content can be measured by the method described in the examples.

The PHA constituting the PHA particles of the present invention is particulate PHA. The shape is not particularly limited as long as it is particulate, and may be any of granular, substantially spherical, spherical, fibrous, needle-like, columnar, rod-like, plate-like, shapes similar to these, irregular shapes and the like. The shape of the PHA particles in the PHA aqueous dispersion of the present invention produced from microbially produced PHA is usually particulate.

(B) Peptidoglycan

Peptidoglycan constituting the PHA particles of the present invention is a polymer of glycopeptide constituting a cell wall component of most prokaryotes such as microorganisms. Peptidoglycan contains N-acetylmuramic acid or N-glycosylmuramic acid and D-amino acid, and glycan chains and peptide chains are linked in a network to construct a three-dimensional structure and thus to form a physically extremely rigid structure.

The peptidoglycan is preferably peptidoglycan of a microorganism that has produced PHA. That is, as the peptidoglycan constituting the PHA particles of the present invention, it is preferable to use peptidoglycan derived from a microorganism that produced PHA while leaving the peptidoglycan as it is.

The content of peptidoglycan in the PHA particles of the present invention is 0.1% by weight or more, preferably 0.2% by weight or more, more preferably 0.5% by weight or more, and 1.0% by weight or less, preferably 0.98% by weight or less, and more preferably 0.95% by weight or less. By setting the content of peptidoglycan to 0.1% by weight or more, an aqueous dispersion having excellent dispersibility and film formation capability can be obtained. On the other hand, by setting the content of peptidoglycan to 1.0% by weight or less, a molded body (such as a thin film) having a good color tone and suppressed odor can be obtained. The content of peptidoglycan in the PHA particles of the present invention can be measured, for example, by the method described in the examples.

(C) Other Components

The PHA particles of the present invention may contain only PHA and peptidoglycan as components and may further contain other components. Representative examples of the other components include impurities derived from microorganisms. Representative examples of the impurities include proteins. The protein is a polymer of amino acids, which is a component constituting most prokaryotes such as microorganisms. Amino acids are linked by peptide bond to form a protein. The protein usually accounts for about 40% of impurities derived from microorganisms except PHA.

The protein content in the PHA particles of the present invention is preferably 1.0% by weight or less and more preferably 0.5% by weight or less. By controlling the protein content to 1.0% by weight or less, coloring of a molded article produced using PHA particles or an aqueous dispersion thereof tends to be suppressed, and odor generation during heating of the molded article tends to be suppressed. The lower limit of the protein content is not particularly limited and is most preferably 0% by weight, but may be, for example, 0.01% by weight or more. The protein content in the PHA particles of the present invention can be measured, for example, as an amount equivalent to bovine serum albumin by the method described in the examples.

The PHA particles of the present invention may further contain impurities derived from microorganisms except proteins and the like. Examples of the impurities include nucleic acids, lipids, polysaccharides and other carbides.

The PHA particles of the present invention can be used in any form. For example, the PHA particles of the present invention can be used in a substantially dry state, or can be used in the form of a dispersion dispersed in a dispersion medium. The particle size of the PHA particles is not particularly limited, and for example, the average particle size of primary particles thereof is preferably 0.05 to 10 more preferably 0.3 to 5.0 μm, and still more preferably 0.5 to 3.0 μm. The above average particle size is determined using a general-purpose particle size meter such as a Microtrac particle size analyzer (manufactured by Nikkiso Co., Ltd.) and measured as a particle size (volume average particle size) with respect to a cumulative amount of 50% of all particles in normal distribution by dispersing PHA particles in water.

[PHA Aqueous Dispersion]

The PHA aqueous dispersion (polyhydroxyalkanoate aqueous dispersion) of the present invention is an aqueous dispersion having at least an aqueous medium and PHA particles (the PHA particles of the present invention) dispersed in the aqueous medium. As described below, the PHA aqueous dispersion of the present invention may contain other components. The "PHA aqueous dispersion" in the present invention is not limited to a dispersion containing water as a medium, and as described later, the "PHA aqueous dispersion" is a term including a dispersion containing an organic solvent compatible with water as a medium.

The concentration of PHA particles in the PHA aqueous dispersion of the present invention is not particularly limited, but is preferably 300 g/L or more, more preferably 400 g/L or more, and still more preferably 500 g/L or more. An upper limit value of the concentration is also not particularly limited, but is preferably 700 g/L or less and more preferably 600 g/L or less. Concerning pH of the aqueous dispersion, it is not particularly limited, but is preferably 4.0 to 9.0 in terms of dispersibility of PHA particles.

Examples of the aqueous medium contained in the aqueous dispersion of the present invention include water, an organic solvent compatible with water, and a mixed solvent of water and the organic solvent. The organic solvent may be used alone or in combination of two or more. The concentration of the organic solvent in the mixed solvent of water and the organic solvent is not particularly limited as long as it is not more than the solubility of the organic solvent used in water. Furthermore, although the organic solvent that is compatible with water is not particularly limited, for example, alcohols such as methanol, ethanol, 1-propanol, 2-propanol, 1-butanol, 2-butanol, iso-butanol, pentanol, hexanol and heptanol; ketones such as acetone and methyl ethyl ketone; ethers such as tetrahydrofuran and dioxane; nitriles such as acetonitrile and propionitrile; amides such as dimethylformamide and acetamide; dimethyl sulfoxide, pyridine, piperidine, and the like may be exemplified. Among these, methanol, ethanol, 1-propanol, 2-propanol, 1-butanol, 2-butanol, iso-butanol, acetone, methyl ethyl ketone, tetrahydrofuran, dioxane, acetonitrile, propionitrile and the like are preferred from the viewpoint of ease of removal and the like. Still further, methanol, ethanol, 1-propanol, 2-propanol, 1-butanol, 2-butanol, iso-butanol, acetone and the like are more preferred in view of favorable availability. Methanol, ethanol, and acetone are still more preferred. It should be noted that other solvent and/or components derived from the cellular bodies and compounds generated during purification may be contained as long as essential features of the present invention are not impaired.

The PHA aqueous dispersion of the present invention may contain other components. Examples of other components include surfactants, dispersants, and preservatives. As the surfactant, anionic surfactants (such as sodium dodecyl sulfate, sodium dodecylbenzene sulfonate, sodium cholate, sodium deoxycholate and sodium oleate) and nonionic surfactants (such as polyoxyethylene alkyl ether and polyoxyalkylene alkyl ether) are preferable in terms of price, amount used and addition effect. Examples of the dispersant include water-soluble polymers such as polyvinyl alcohol, methyl cellulose, ethyl cellulose, hydroxymethyl cellulose, hydroxyethyl cellulose, polyacrylic acid, sodium polyacrylate, potassium polyacrylate, polymethacrylic acid, and sodium polymethacrylate. Among them, polyvinyl alcohol and methyl cellulose are preferred. Examples of the preservative include hydrogen peroxide, potassium sorbate, sodium benzoate, hinokitiol, and paraben.

The average particle size of PHA particles in the PHA aqueous dispersion of the present invention is not particularly limited and is preferably 0.05 to 10 μm, more preferably 0.3 to 5.0 μm, and still more preferably 0.5 to 3.0 μm. The above average particle size is determined using a general-purpose particle size meter such as a Microtrac particle size analyzer (manufactured by Nikkiso Co., Ltd.) and measured as a particle size (volume average particle size) with respect to the cumulative amount of 50% of all particles in normal distribution by using a PHA aqueous dispersion as a measurement sample. When the average particle size is in the above range, a handling property, water dispersibility and film formation capability tend to be further improved.

(Method of Producing PHA Particles and PHA Aqueous Dispersion)

The PHA particles of the present invention are not particularly limited and can be produced by a production method using a known or conventional technique. Examples of the production method includes a method including a step in which, with respect to microorganisms accumulating PHA in their cells (microorganisms having the ability to produce PHAs), components (particularly organic substances) derived from microorganisms except PHA are decomposed, solubilized and/or removed, and then particulate PHA is recovered. In this method, in order to remove other impurities while leaving a predetermined amount (0.1% by weight or more and 1.0% by weight or less) of peptidoglycan derived from the cell wall of the microorganism, for example, it is preferable to use no cell wall degrading enzyme or reduce the amount used; set pressure during high-pressure disruption to a range that is neither too low nor too high; control time of high-pressure disruption; or combine and control these processes. The pressure during high-pressure disruption is not particularly limited, but is preferably 100 to 500 kg/cm$^2$.

As a method of decomposing, solubilizing and/or removing impurities such as components derived from microorganisms except PHA particles in the above production method, a method of physically treating, chemically treating or biologically treating PHA-containing cells is preferred. Thereby, the process of degradation and/or removal of impurities of components derived from microorganisms can be efficiently carried out. Although the physical treatment method, the chemical treatment method, or the biological treatment method is not particularly limited, any process carried out using fluid shearing force or solid shearing force, or by grinding, by means of a conventionally well-known French press, high-pressure homogenizer, X-press, ball mill, colloid mill, DYNO mill, ultrasonic homogenizer or the like may be employed. In a case of using a high-pressure homogenizer, when operating pressure is increased, there is a tendency to reduce impurities derived from microorganisms, so that it is preferable that the operating pressure be adjusted such that peptidoglycan is 0.1% by weight or more, protein is 1.0% by weight or less, and PHA is 98% by weight or more.

Alternatively, a process in which an agent such as an acid, alkali, surfactant, organic solvent, cell wall synthesis inhibitor or the like is used, a process in which an enzyme such as protease, pectinase, or zymolyase is used, a process in which supercritical fluid is used, an osmotic disruption process, a freezing process, a dry disruption process, and the like may be exemplified. Also, an autolysis process carried out using an action of protease, esterase, etc., included in the cells per se is also exemplified as one type of disruption process. In these disruption processes, to select a process capable of inhibiting lowering of the molecular weight of PHA by a series of treatments is desired. In addition, these disruption processes may be used either alone, or a plurality of the processes may be used in combination. Also, either batchwise processing, or continuous processing may be conducted.

The process of degradation and/or removal of impurities such as components derived from microorganisms except PHA particles is not particularly limited, and for example, a process carried out using an enzyme may be exemplified. The enzyme which may be used includes a proteolytic enzyme, a lipolytic enzyme, cell wall degrading enzyme, nucleolytic enzyme, and the like. Specific examples of these enzymes include the followings. These may be used either alone, or two or more of these may be used in combination.

(1) Proteolytic Enzyme
Esperase, Alcalase, pepsin, trypsin, papain, chymotrypsin, aminopeptidase, carboxypeptidase, and the like (2) Lipolytic Enzyme
lipase, phospholipase, cholineesterase, phosphatase, and the like (3) Nucleic Acid Degrading Enzyme
ribonuclease, deoxyribonuclease, and the like The enzyme used in degradation of impurities such as components derived from microorganisms except PHA particles is not limited to those described above, and may be an arbitrary enzyme having an activity of degradation of components derived from microorganisms as long as it can be used in industrial products. Also, a commercially available enzyme detergent used for washing or the like in general may be also used. Still further, an enzyme composition containing, for example, a stabilizing agent of an enzyme, an antisoil redeposition agent, etc., and the enzyme is also acceptable, and it is not necessarily limited to use of only an enzyme. Preferable proteolytic enzymes which may be industrially used include, among the above-illustrated enzymes, protease A, protease P, protease N (all manufactured by Amano Enzyme inc.), Esperase, Alcalase, Savinase, Everlase (all manufactured by Novozymes A/S), and the like, and these can be suitably used also in light of the degradation activity, but not limited thereto.

On the other hand, the cell wall degrading enzyme may be used in such a range that the content of peptidoglycan contained in PHA particles can be controlled to be 0.1% by weight or more.

(1) Cell Wall Degrading Enzyme
lysozyme, amylase, cellulase, maltase, saccharase, α-glycosidase, β-glycosidase, N-glycosidase, and the like The enzyme treatment is preferably carried out until a desired degree of the treatment is achieved, and the time period is usually 0.5 to 2 hours. The amount of the enzyme to be used depends on the type and activity of the enzyme, and is not particularly limited, but is preferably 0.001 to 10 parts by weight, and in light of the cost, more preferably 0.001 to 5 parts by weight relative to 100 parts by weight of PHA particles.

Other process for the degradation of impurities such as components other than PHA particles derived from the organism includes a process in which hypochlorous acid or hydrogen peroxide is used. When hypochlorous acid is used, the pH of the system is adjusted to fall within an alkaline region, and hypochlorous acid treatment is executed under conditions in which heat, light, or contact with metal can be inhibited, whereby PHA particles having a low amount of remaining chlorine can be obtained. The pH of the system is desirably 8 or more, more desirably 10 or more, and further desirably 12 or more. The treatment temperature is desirably 40° C. or less, more desirably 30° C. or less, still more desirably 20° C. or less, and for surely achieving the effects, the treatment is carried out at 10° C. or less.

In general, an aqueous PHA suspension prepared by physically, chemically, or biologically treating PHA-containing cellular bodies according to the aforementioned process is contaminated with proteins, nucleic acids, lipids and sugar components in cells, and other constitutive components of cellular bodies, culture substrate residues, and the like. It is preferred to carry out a dehydration step for separating water containing these proteins and the like. Accordingly, the amount of impurities included in the aqueous PHA suspension can be reduced. Although dehydration process is not particularly limited, process of filtration, centrifugal separation, or precipitation separation may be exemplified.

As described above, in the aforementioned dehydration step, for separating PHA particles from water containing impurities such as other components derived from the organism, filtration, centrifugal separation or the like may be carried out. Although the filtration process is not particularly limited, a process carried out using Nutsche or the like, or process such as suction filtration or pressure filtration is desired. For industrial applications, filtration equipment having a compressing function such as a filter press, tube press, plate press, gauge press, belt press, screw press or disk press, as well as a centrifugal dehydrator, a multiple cylindrical filtration element or the like may be selected. When improving productivity is intended, a continuous type filtration element such as a multiple cylindrical filtration element is desired. As a process for removing scums of particles in a continuous type filtration element, a string system, a scraper system, a precoating scraper system or the like may be involved. Alternatively, a membrane separation system may be also employed. As a process for filtration involving membrane separation, dead end filtration, or cloth flow filtration may be selected. Any case may be selected based on the filterability, the extent of clogging of the filter material, membrane and the like. In addition, reduced pressure or vacuum may be provided, or compression may be permitted. Furthermore, a process in which centrifugal force is employed may be used. As a filter material, any of a variety of materials such as a paper, woven fabric, nonwoven fabric, screen, sintered plate, unglazed pottery, polymer membrane, punching metal or wedge wire may be selected. Any one may be selected depending upon the productivity and degree of clogging and the like. Also, a filter aid may or may not be used. When a filter aid is used, either a process of precoating the filter aid onto the filter material beforehand (i.e., precoating system), or a process of previously adding to a liquid subjected to the filtration (i.e., body feeding method) may be employed.

Although the process of centrifugal separation in the aforementioned dehydration step is not particularly limited, a centrifugal settler, a centrifugal dehydrator or the like may be used. In the case of a centrifugal settler, a separator type, a cylindrical type, and a decanter type may be exemplified. In the case of the separator type, a disk type, a self cleaning type, a nozzle type, a screw decanter type, a skimming type, and the like may be exemplified. Depending on the procedure of discharging precipitated components, there are batch type and continuous type, respectively. Also, with respect to the centrifugal dehydrator, there may be batch type and continuous type. Separation of precipitates containing PHA particles from culture liquid components is enabled with these equipments, based on the difference in specific gravity.

Other process which may be used in the above dehydration step may include a floatation process, an electrophoresis process, a cyclone processing, and the like. The processes of filtration and centrifugal separation, as well as floatation may be used alone, or in combination.

After PHA particles were recovered by the process such as filtration and/or centrifugal separation in the aforementioned dehydration step, the recovered PHA particles are washed with an aqueous medium such as water, whereby further purified PHA particles can be obtained. The washing may be carried out using not only water but also an organic solvent, and water and an organic solvent may be used as a mixture. Also, the pH of water may be adjusted. When an organic solvent is used as a washing solvent, preferably, a hydrophilic solvent, and more specifically methanol, ethanol, acetone, acetonitrile, tetrahydrofuran, a ketone, an amine or the like may be used. In addition, a surfactant or the like may be added to water. A plurality of types of these organic solvents and water may be used as a mixture. Moreover, water or the organic solvent may be heated or sprayed in the form of vapor to improve the washing property as long as this process is carried out within a short period of time.

A method for producing the PHA particles of the present invention may include a step of obtaining the above-mentioned microorganism accumulating PHA in the cell (step of culturing the microorganism having the ability to produce PHAs to produce PHA). Each process in the method of producing the PHA particles of the present invention may be implemented continuously or discontinuously.

The PHA aqueous dispersion of the present invention can be produced, for example, by dispersing PHA particles obtained by the above-mentioned method in an aqueous medium to a predetermined concentration. The method of dispersing PHA particles is not particularly limited, and known or conventional dispersing means such as a method using a stirrer and a homogenizer can be used. It is preferable that the PHA particles to be dispersed in an aqueous medium be in a wet state after being washed with the aqueous medium from the viewpoint of ease of production of an aqueous dispersion.

The PHA particles of the present invention and the PHA aqueous dispersion of the present invention can be used for various applications and are not particularly limited, and for example, they can be used in applications for obtaining various molded bodies by subjecting them to known or conventional molding methods. In particular, since the aqueous dispersion of the present invention is excellent in film formation capability, films (coated layer) of PHA, films and the like can be obtained by applying the aqueous dispersion on a substrate (for example, a substrate of metal, paper, plastic, fiber or the like) followed by drying.

EXAMPLES

Hereinafter, the present invention is explained in more detail based on Examples, but the present invention is not limited to the Examples.

Production Example 1

Preparation of Cell Culture Solution Containing PHA

KNK-631 strain (see WO 2009/145164) was used for culture production.

The composition of a seed medium was: 1 w/v % Meat-extract, 1 w/v % Bacto-Tryptone, 0.2 w/v % Yeast-extract, 0.9 w/v % $Na_2HPO_4.12H_2O$, 0.15 w/v % $KH_2PO_4$, (pH 6.8).

The composition of a preculture medium was: 1.1 w/v % $Na_2HPO_4.12H_2O$, 0.19 w/v % $KH_2PO_4$, 1.29 w/v % $(NH_4)_2SO_4$, 0.1 w/v % $MgSO_4.7H_2O$, and 0.5 v/v % trace metal salt solution (prepared by dissolving, in 0.1 N hydrochloric acid, 1.6 w/v % $FeCl_3.6H_2O$, 1 w/v % $CaCl_2.2H_2O$, 0.02 w/v % $CoCl_2.6H_2O$, 0.016 w/v % $CuSO_4.5H_2O$, and 0.012 w/v % $NiCl_2.6H_2O$). Palm oil was used as a carbon source and added at one time at a concentration of 10 g/L.

The composition of the PHA production medium was: 0.385 w/v % $Na_2HPO_4.12H_2O$, 0.067 w/v % $KH_2PO_4$, 0.291 w/v % $(NH_4)_2SO_4$, 0.1 w/v % $MgSO_4.7H_2O$, 0.5 v/v % trace metal salt solution (prepared by dissolving, in 0.1 N hydrochloric acid, 1.6 w/v % $FeCl_3.6H_2O$, 1 w/v % $CaCl_2.2H_2O$, 0.02 w/v % $CoCl_2.6H_2O$, 0.016 w/v % $CuSO_4.5H_2O$, 0.012 w/v % $NiCl_2.6H_2O$), and 0.05 w/v % BIOSPUREX200K (defoaming agent: manufactured by Cognis Japan Ltd.).

First, a glycerol stock (50 μl) of KNK-631 strain was inoculated into the seed medium (10 ml) and seed-cultured for 24 hours. Then, the resulting seed culture solution was inoculated at 1.0 v/v % into a 3-liter jar fermenter (MDL-300 manufactured by B. E. MARUBISHI Co., Ltd.) containing 1.8 L of the preculture medium. Preculture was performed for 28 hours under operation conditions where a culture temperature was 33° C., a stirring speed was 500 rpm, and a ventilation volume was 1.8 L/min while pH was controlled to be in the range of 6.7 to 6.8. The pH control was performed by using a 14% aqueous ammonium hydroxide solution.

Then, the resulting preculture solution was inoculated at 1.0 v/v % into a 10-liter jar fermenter (MDS-1000 manufactured by B. E. MARUBISHI Co., Ltd.) containing 6 L of the PHA production medium. Culture was performed under operation conditions where a culture temperature was 28° C., a stirring speed was 400 rpm, and a ventilation volume was 6.0 L/min while pH was controlled to be in the range of 6.7 to 6.8. The pH control was performed by using a 14% aqueous ammonium hydroxide solution. As described above, palm oil was used as a carbon source in the culture. The culture was performed for 64 hours to obtain a cell culture solution containing PHBH as PHA.

The cell culture solution containing PHA obtained above was centrifuged to recover cells, washed with methanol, and freeze-dried to obtain dry cell bodies. When the weight of the dry cell bodies was measured, with the result that the weight of the dry cell bodies was 230 g/L, and the PHA concentration was 70%. A 3HH (3-hydroxyhexanoate) composition ratio, the degree of crystallinity, and the average molecular weight of PHA in the cell culture solution containing PHA obtained above were measured according to the following methods, with the result that the 3HH composition ratio was 11.5 mol %, the degree of crystallinity was 30%, and the average molecular weight of PHA was 1.2 million.

(Method of Measuring 3HH Composition Ratio of PHA)

To 1 g of the dry cell bodies obtained by the above method was added chloroform in an amount of 100 ml. At room temperature, the resultant was stirred a whole day and night. PHA in the cell bodies was extracted. The cell body residue was filtered, and subjected to an evaporator to concentrate the residue until the total volume thereof was 30 ml. Thereto was then gradually added hexane in an amount of 90 ml. The liquid was allowed to stand still for 1 hour while slowly stirred. The precipitated PHA was filtered and then vacuum-dried at 50° C. for 3 hours to obtain purified PHA.

3HH composition ratio analysis of the obtained purified PHA was measured by gas chromatography as follows. 2 ml of a mixed solution of sulfuric acid and methanol (15:85) and 2 ml of chloroform were added to 20 mg of the purified PHA, and the mixture was hermetically sealed and heated at 100° C. for 140 minutes to obtain a methyl ester of PHA degradation product. After cooled, the methyl ester of PHA degradation product was neutralized by adding 1.5 g of sodium hydrogen carbonate little by little, and the mixture was allowed to stand until the generation of carbon dioxide was stopped. The mixture was added and well mixed with 4 ml of diisopropyl ether and then centrifuged, and then a monomer unit composition ratio of a polyester degradation product in the supernatant was analyzed by capillary gas chromatography "GC-17A" manufactured by Shimadzu Corporation and a capillary column "NEUTRA BOND-1" manufactured by GL Sciences Inc. (column length: 25 m, column inner diameter: 0.25 mm, liquid membrane thickness: 0.4 μm).

(Method of Measuring Degree of Crystallinity of PHA)

The temperature of the purified PHA obtained by the above method was increased at 10° C./min from 25° C. to a temperature higher than the melting point of the resin and held for 2 minutes using DSC (DSC 220 manufactured by Sii Nanotechnology Inc.), and after the resin was melted, cooling was performed at 10° C./min. The degree of crystallinity was evaluated according to the temperature and magnitude (heat of crystallization) of a peak showing crystallization, which was observed in the cooling process.

(Method of Measuring Weight-Average Molecular Weight of PHA)

With respect to the purified PHA obtained by the above method, a molecular weight based on polystyrene standards was measured using a gel permeation chromatograph ("Shodex GPC-101" manufactured by Showa Denko K.K.), a polystyrene gel column ("Shodex K-804" manufactured by Showa Denko K.K.), and chloroform as a mobile phase, and the weight-average molecular weight was calculated from the molecular weight.

Production Example 2

A cell culture solution containing PHBH as PHA was obtained in the same manner as in Production Example 1, except that KNK-005 strain was used instead of KNK-631 strain.

With respect to the cell culture solution containing PHA obtained above, the weight of the dry cell bodies was measured in the same manner as in Production Example 1, with the result that the weight of the dry cell bodies was 250 g/L and the PHA concentration was 80%. In addition, the 3HH composition ratio, the degree of crystallinity, and the weight-average molecular weight of PHA were measured in the same manner as in Production Example 1, with the result that the 3HH composition ratio was 5.8 mol %, the degree of crystallinity was 40%, and the weight-average molecular weight was 1.5 million.

Production Example 3

A cell culture solution containing PHBH as PHA was obtained by the method described in Production Example 1, except that KNK-252 strain was used instead of KNK-631 strain and PFAD (Palm Fatty Acid Distillate) was used as a carbon source, instead of palm oil.

With respect to the cell culture solution containing PHA obtained above, the weight of the dry cell bodies was measured in the same manner as in Production Example 1, with the result that the weight of the dry cell bodies was 255 g/L and the PHA concentration was 82%. In addition, the 3HH composition ratio, the degree of crystallinity, and the weight-average molecular weight of PHA were measured in the same manner as in Production Example 1, with the result that the 3HH composition ratio was 16.9 mol %, the degree of crystallinity was 26%, and the weight-average molecular weight was 1.2 million.

Example 1

The cell culture solution containing PHA obtained in Production Example 1 was heated at 80° C. for 1 hour and sterilized. Next, thereto was added protease in an amount of 1/100 by weight of PHA (manufactured by Novozymes A/S, Esperase), and the mixture was stirred for 2 hours while maintaining the pH of 8.0 at 50° C. Thereafter, to this liquid was added a 30% aqueous solution of sodium dodecyl sulfate so that the concentration of sodium dodecyl sulfate was 1.0% by weight, and a 30% aqueous solution of sodium hydroxide was further added so that the pH was 11.5. Thereafter, temperature was kept at 50° C. for 1 hour. Thereafter, disruption at high pressure was carried out with a high-pressure disrupting machine (high-pressure homogenizer model PA2K manufactured by Niro Soavi S.P.A) at a pressure of about 200 kgf/cm$^2$. The disruption liquid after high-pressure disruption was subjected to centrifugation, and the supernatant was then removed. With respect to the resultant precipitate, washing with water by centrifugation was further repeated six times, and water was added to the finally obtained precipitate to adjust the PHA particle concentration to 50% and thus to obtain a PHA aqueous dispersion. The PHA particles contained in the aqueous dispersion were those in which the particle surface was coated with peptidoglycan.

The average particle size of the PHA particles in the aqueous dispersion was measured by Microtrac MT3300EXII (manufactured by Nikkiso Co., Ltd.). The aqueous dispersion diluted down to about 100 times was observed at 300 times magnification by a H550S lens manufactured by Nikon Corporation. A photograph taken is shown in FIG. 1.

Figure 2:
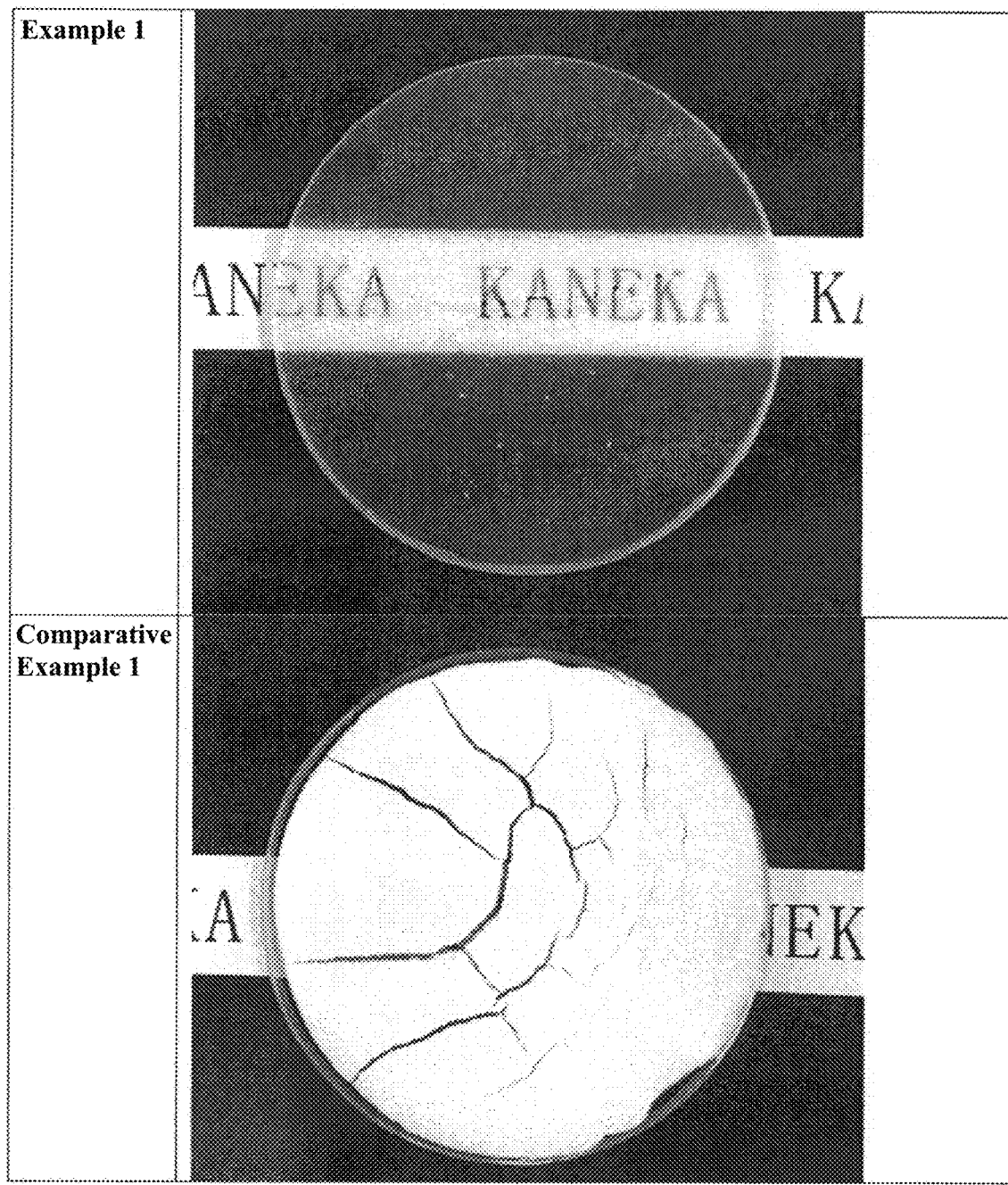
FIG. 2 is photographs of thin films produced in Example 1 and Comparative Example 1.

The obtained aqueous dispersion was dehydrated by Nutsche and then heated and dried under reduced pressure to obtain a dry sample of PHA particles, and the amount of PHA, the amount of protein and the amount of peptidoglycan in the PHA particles were determined by the methods described later. 1 to 3 g of the obtained aqueous dispersion was thinly applied to a bottom of a glass plate of φ 800 mm, and water was evaporated in an oven heated to 120° C. After it was confirmed that water was sufficiently evaporated, cooling was performed, and it was confirmed that a thin film of PHA was formed on a surface of the glass plate. The appearance and odor of the obtained thin film were confirmed. The results are shown in Table 1. A photograph of the obtained thin film is shown in FIG. 2.

Example 2

The cell culture solution containing PHA obtained in Production Example 2 was heated at 80° C. for 1 hour and sterilized. Thereafter, to this liquid was added a 30.0% aqueous solution of sodium dodecyl sulfate so that the concentration of sodium dodecyl sulfate was 1.0% by weight, and a 30% aqueous solution of sodium hydroxide was further added so that the pH was 11.5. Thereafter, temperature was kept at 50° C. for 1 hour. Thereafter, disruption at high pressure was carried out with a high-pressure disrupting machine (high-pressure homogenizer model PA2K manufactured by Niro Soavi S.P.A) at a pressure of about 200 kgf/cm$^2$. The disruption liquid after high-pressure disruption was subjected to centrifugation, and the supernatant was then removed. With respect to the resultant precipitate, washing with water by centrifugation was further repeated six times, and water was added to the finally obtained precipitate to adjust the PHA particle concentration to 50% and thus to obtain a PHA aqueous dispersion. The PHA particles contained in the aqueous dispersion were those in which the particle surface was coated with peptidoglycan.

The average particle size of the PHA particles in the aqueous dispersion was measured by Microtrac MT3300EXII (manufactured by Nikkiso Co., Ltd.). The obtained aqueous dispersion was dehydrated by Nutsche and then heated and dried under reduced pressure to obtain a dry sample of PHA particles, and the amount of PHA, the amount of protein and the amount of peptidoglycan in the PHA particles were determined by the methods described later. 1 to 3 g of the obtained aqueous dispersion was thinly applied to a bottom of a glass plate of φ 800 mm, and water was evaporated in an oven heated to 120° C. After it was confirmed that water was sufficiently evaporated, cooling was performed, and it was confirmed that a thin film of PHA was formed on a surface of the glass plate. The appearance and odor of the obtained thin film were confirmed. The results are shown in Table 1.

Example 3

The cell culture solution containing PHA obtained in Production Example 3 was heated at 80° C. for 1 hour and sterilized. Thereafter, to this liquid was added a 30.0% aqueous solution of sodium dodecyl sulfate so that the concentration of sodium dodecyl sulfate was 1.0% by weight, and a 30% aqueous solution of sodium hydroxide was further added so that the pH was 11.5. Thereafter, temperature was kept at 50° C. for 1 hour. Thereafter, disruption at high pressure was carried out with a high-pressure disrupting machine (high-pressure homogenizer model PA2K manufactured by Niro Soavi S.PA) at a pressure of about 200 kgf/cm$^2$. The disruption liquid after high-pressure disruption was subjected to centrifugation, and the supernatant was then removed. With respect to the resultant precipitate, washing with water by centrifugation was further repeated six times, and water was added to the finally obtained precipitate to adjust the PHA particle concentration to 50% and thus to obtain a PHA aqueous dispersion. The PHA particles contained in the aqueous dispersion were those in which the particle surface was coated with peptidoglycan.

The average particle size of the PHA particles in the aqueous dispersion was measured by Microtrac MT3300EXII (manufactured by Nikkiso Co., Ltd.). The obtained aqueous dispersion was dehydrated by Nutsche and then heated and dried under reduced pressure to obtain a dry sample of PHA particles, and the amount of PHA, the amount of protein and the amount of peptidoglycan in the PHA particles were determined by the methods described later. 1 to 3 g of the obtained aqueous dispersion was thinly applied to a bottom of a glass plate of φ 800 mm, and water was evaporated in an oven heated to 120° C. After it was confirmed that water was sufficiently evaporated, cooling was performed, and it was confirmed that a thin film of PHA was formed on a surface of the glass plate. The appearance and odor of the obtained thin film were confirmed. The results are shown in Table 1.

(Method of Calculating Amount of PHA in PHA Particles)

The aqueous dispersion obtained above was dehydrated by Nutsche and then heated and dried under reduced pressure to obtain a dry sample. 5 mg of the dry sample was heated from the room temperature to 600° C. with TG-DTA (manufactured by Sii Nanotechnology Inc.), and the PHA amount was determined from the remaining weight at 300 to 320° C. with respect to the weight before heating.

(Method of Calculating Amount of Peptidoglycan in PHA Particles)

To the aqueous dispersion obtained above was added a solution prepared by SLP-HS Single Reagent Set manufactured by Wako Pure Chemical Industries, Ltd., and the absorbance (650 nm) of the mixture was measured at 30° C. for 120 minutes by Power Scan HT (manufactured by DS Pharma Biomedical Co., Ltd.). A calibration curve was prepared from the absorbance of peptidoglycan adjusted to a known concentration, and the amount of peptidoglycan contained in PHA was determined by comparison with the measured absorbance of the aqueous dispersion.

(Method of Calculating Amount of Protein Remaining in PHA Particles)

The aqueous dispersion obtained above was dehydrated by Nutsche and then heated and dried under reduced pressure to obtain a dry sample. After 1 mg of the dry sample was suspended in 1 ml of distilled water, a solution prepared by BCA™ Protein Assay Kit manufactured by Takara Bio Inc. was added and treated at 60° C. for 30 minutes. The mixture was cooled and then analyzed using an absorbance meter UV-1700 manufactured by Shimadzu Corporation, and the amount of protein remaining in PHA particles was determined in terms of bovine serum albumin.

(Evaluation of Dispersibility of PHA Aqueous Dispersion)

The dispersibility of the PHA aqueous dispersion obtained above was evaluated based on the following criteria.

Good (good dispersibility): the average particle size is in the range of 0.05 to 10 μm Poor (poor dispersibility): the average particle size is more than 10 μm (Evaluation of Film Formation Capability of PHA Aqueous Dispersion)

The film formation capability of the PHA aqueous dispersion obtained above was evaluated by visually observing the thin film formed by the method described above. When a uniform semi-transparent film or transparent film is obtained, it can be evaluated that the film formation capability is excellent (that is, the dispersion is capable of forming a good film).

(Odor Evaluation)

The odor of the thin film formed by the method described above was smelled, and the presence or absence of the odor was evaluated.

(Comparative Example 1)

The cell culture solution containing PHA obtained in Production Example 1 was heated at 80° C. for 1 hour and sterilized. Next, thereto was added protease in an amount of 1/100 by weight of PHA (manufactured by Novozymes A/S, Esperase), and the mixture was stirred for 2 hours while maintaining the pH of 8.0 at 50° C. Thereafter, to this liquid was added a 30% aqueous solution of sodium dodecyl sulfate so that the concentration of sodium dodecyl sulfate was 1.0% by weight, and a 30% aqueous solution of sodium hydroxide was further added so that the pH was 11.5. Thereafter, temperature was kept at 50° C. for 1 hour. Thereafter, disruption at high pressure was carried out with a high-pressure disrupting machine (high-pressure homogenizer model PA2K manufactured by Niro Soavi S.P.A) at a pressure of about 550 kgf/cm². The disruption liquid after high-pressure disruption was subjected to centrifugation, and the supernatant was then removed. With respect to the resultant precipitate, washing with water by centrifugation was further repeated six times, and water was added to the finally obtained precipitate to adjust the PHA particle concentration to 30% and thus to obtain a PHA aqueous dispersion.

The average particle size of the PHA particles in the aqueous dispersion was measured by Microtrac MT3300EXII (manufactured by Nikkiso Co., Ltd.). The aqueous dispersion diluted down to about 100 times was observed at 300 times magnification by a H550S lens manufactured by Nikon Corporation. A photograph taken is shown in FIG. 1.

The obtained aqueous dispersion was dehydrated by Nutsche and then heated and dried under reduced pressure to obtain a dry sample of PHA particles, and the amount of PHA, the amount of protein and the amount of peptidoglycan in the PHA particles were determined by the methods described above. 1 to 3 g of the obtained aqueous dispersion was thinly applied to a bottom of a glass plate of φ 800 mm, and water was evaporated in an oven heated to 120° C. After it was confirmed that water was sufficiently evaporated, cooling was performed, and it was confirmed that a thin film of PHA was formed on a surface of the glass plate. The appearance and odor of the obtained thin film were confirmed. The results are shown in Table 1. A photograph of the obtained thin film is shown in FIG. 2.

Comparative Example 2

The cell culture solution containing PHA obtained in Production Example 1 was heated at 80° C. for 1 hour and sterilized. Next, thereafter, to this liquid was added a 30.0% aqueous solution of sodium dodecyl sulfate so that the concentration of sodium dodecyl sulfate was 1.0% by weight, and a 30% aqueous solution of sodium hydroxide was further added so that the pH was 11.5. Thereafter, temperature was kept at 50° C. for 1 hour. Thereafter, disruption at high pressure was carried out with a high-pressure disrupting machine (high-pressure homogenizer model PA2K manufactured by Niro Soavi S.PA) at a pressure of about 10 kgf/cm². The disruption liquid after high-pressure disruption was subjected to centrifugation, and the supernatant was then removed. With respect to the resultant precipitate, washing with water by centrifugation was further repeated six times, and water was added to the finally obtained precipitate to adjust the PHA particle concentration to 50% and thus to obtain a PHA aqueous dispersion.

The average particle size of the PHA particles in the aqueous dispersion was measured by Microtrac MT3300EXII (manufactured by Nikkiso Co., Ltd.). The obtained aqueous dispersion was dehydrated by Nutsche and then heated and dried under reduced pressure to obtain a dry sample of PHA particles, and the amount of PHA, the amount of protein and the amount of peptidoglycan in the PHA particles were determined by the methods described above. 1 to 3 g of the obtained aqueous dispersion was thinly applied to a bottom of a glass plate of φ 800 mm, and water was evaporated in an oven heated to 120° C. After it was confirmed that water was sufficiently evaporated, cooling was performed, and it was confirmed that a thin film of PHA was formed on a surface of the glass plate. The appearance and odor of the obtained thin film were confirmed. The results are shown in Table 1.

Comparative Example 3

The cell culture solution containing PHA obtained in Production Example 2 was heated at 80° C. for 1 hour and sterilized. Next, to this liquid was added a 30.0% aqueous solution of sodium dodecyl sulfate so that the concentration of sodium dodecyl sulfate was 1.0% by weight, and a 30% aqueous solution of sodium hydroxide was further added so that the pH was 11.5. Thereafter, temperature was kept at 50° C. for 1 hour. Thereafter, disruption at high pressure was carried out with a high-pressure disrupting machine (high-pressure homogenizer model PA2K manufactured by Niro Soavi S.P.A) at a pressure of about 10 kgf/cm$^2$. The disruption liquid after high-pressure disruption was subjected to centrifugation, and the supernatant was then removed. With respect to the resultant precipitate, washing with water by centrifugation was further repeated six times, and water was added to the finally obtained precipitate to adjust the PHA particle concentration to 50% and thus to obtain a PHA aqueous dispersion.

The average particle size of the PHA particles in the aqueous dispersion was measured by Microtrac MT3300EXII (manufactured by Nikkiso Co., Ltd.). The obtained aqueous dispersion was dehydrated by Nutsche and then heated and dried under reduced pressure to obtain a dry sample of PHA particles, and the amount of PHA, the amount of protein and the amount of peptidoglycan in the PHA particles were determined by the methods described above. 1 to 3 g of the obtained aqueous dispersion was thinly applied to a bottom of a glass plate of φ 800 mm, and water was evaporated in an oven heated to 120° C. After it was confirmed that water was sufficiently evaporated, cooling was performed, and it was confirmed that a thin film of PHA was formed on a surface of the glass plate. The appearance and odor of the obtained thin film were confirmed. The results are shown in Table 1.

was odorous. In Comparative Example 3, the film formability was poor, and the thin film formed was white and opaque and was odorous.

The invention claimed is:

1. A polyhydroxyalkanoate particle, comprising:
polyhydroxyalkanoate having a particle shape; and
peptidoglycan covering a portion of or an entire surface of the polyhydroxyalkanoate,
wherein the polyhydroxyalkanoate is polyhydroxyalkanoate having a degree of crystallinity of 30% or less, and a content of the polyhydroxyalkanoate is 98.0% by weight or more, and a content of the peptidoglycan is from 0.2% by weight to 1.0% by weight.

2. The polyhydroxyalkanoate particle according to claim 1, wherein the polyhydroxyalkanoate particle contains 1.0% by weight or less of a protein.

3. A polyhydroxyalkanoate aqueous dispersion, comprising:
an aqueous medium; and
a plurality of the polyhydroxyalkanoate particles of claim 1 dispersed in the aqueous medium.

4. The polyhydroxyalkanoate aqueous dispersion of claim 3, wherein an average particle size of the polyhydroxyalkanoate particles dispersed in the aqueous medium is from 0.05 µm to 10 µm.

5. The polyhydroxyalkanoate particle according to claim 1, wherein the polyhydroxyalkanoate is poly(3-hydroxybutyrate-co-3-hydroxyhexanoate) having a 3-hydroxyhexanoate composition ratio of 15 mol % or more.

6. The polyhydroxyalkanoate particle according to claim 1, wherein the content of the polyhydroxyalkanoate is from 98.5% by weight to 99.9% by weight, and the content of the peptidoglycan is from 0.2% by weight to 0.98% by weight.

7. The polyhydroxyalkanoate particle according to claim 1, wherein the content of the polyhydroxyalkanoate is from 99.0% by weight to 99.5% by weight, and the content of the peptidoglycan is from 0.5% by weight to 0.95% by weight.

8. The polyhydroxyalkanoate aqueous dispersion according to claim 3, wherein the aqueous medium comprises

TABLE 1

|  | PHBH wt % | Protein wt % | Peptidoglycan wt % | Particle size (D50) µm | Dispersibility | Film formation capability | Odor |
|---|---|---|---|---|---|---|---|
| Example 1 | 99.0 | 0.17 | 0.75 | 1.3 | Good | Uniform semi-transparent film | A (absence) |
| Example 2 | 98.7 | 0.22 | 0.9 | 1.5 | Good | Uniform semi-transparent film | A |
| Example 3 | 98.9 | 0.14 | 0.9 | 1.8 | Good | Uniform transparent film | A |
| Comparative Example 1 | 99.6 | 0.06 | 0.06 | 10.4 | Poor | Cracked and white | A |
| Comparative Example 2 | 91.8 | 1.4 | 3.1 | 1.3 | Good | With brown insoluble matter, strong yellowish color | P (presence) |
| Comparative Example 3 | 92.9 | 1.21 | 0.9 | 1.5 | Good | White and opaque | P |

As is clear from Table 1, in Examples 1 to 3, the PHA aqueous dispersion has good dispersibility, and excellent film formability to be capable of forming a uniform semi-transparent film or transparent film, and the formed thin film was not odorous. On the other hand, in Comparative Example 1, the dispersibility of the PHA aqueous dispersion was poor, the film formability was also poor, and the thin film formed was cracked and was white and opaque as shown in FIG. 2. In Comparative Example 2, the film formability was poor, and the formed thin film contained brown insoluble matter, had a strong yellowish color, and water and at least one selected from the group consisting of methanol, ethanol, 1-propanol, 2-propanol, 1-butanol, 2-butanol, iso-butanol, acetone, methyl ethyl ketone, tetrahydrofuran, dioxane, acetonitrile, and propionitrile.

9. The polyhydroxyalkanoate aqueous dispersion according to claim 3, wherein the aqueous medium comprises water and at least one selected from the group consisting of methanol, ethanol, 1-propanol, 2-propanol, 1-butanol, 2-butanol, iso-butanol, and acetone.

10. The polyhydroxyalkanoate aqueous dispersion according to claim 3, wherein the average particle size of the polyhydroxyalkanoate particles dispersed in the aqueous medium is from 0.3 μm to 5.0 μm.

11. The polyhydroxyalkanoate aqueous dispersion according to claim 3, wherein the average particle size of the polyhydroxyalkanoate particles dispersed in the aqueous medium is from 0.5 μm to 3.0 μm.

* * * * *